US010286138B2

(12) United States Patent
Becker et al.

(10) Patent No.: US 10,286,138 B2
(45) Date of Patent: May 14, 2019

(54) DIALYSIS BLOODLINE SET AND METHOD OF USE

(71) Applicant: Oxyless Limited, London (GB)

(72) Inventors: Franz Ferdinand Becker, Rodgau (DE); William Kilgallon, London (GB); Amelia Jane Fairburn-Beech, London (GB)

(73) Assignee: OXYLESS LIMITED, London (GB)

( * ) Notice: Subject to any disclaimer, the term of this patent is extended or adjusted under 35 U.S.C. 154(b) by 0 days.

(21) Appl. No.: 15/577,923

(22) PCT Filed: Jun. 6, 2016

(86) PCT No.: PCT/GB2016/051660
§ 371 (c)(1),
(2) Date: Nov. 29, 2017

(87) PCT Pub. No.: WO2016/198841
PCT Pub. Date: Dec. 15, 2016

(65) Prior Publication Data
US 2018/0161488 A1    Jun. 14, 2018

(30) Foreign Application Priority Data
Jun. 8, 2015    (GB) .................................. 1509911.2

(51) Int. Cl.
*A61M 1/36*    (2006.01)

(52) U.S. Cl.
CPC ........ *A61M 1/3652* (2014.02); *A61M 1/3626* (2013.01); *A61M 1/3627* (2013.01);
(Continued)

(58) Field of Classification Search
CPC .............. A61M 1/3626; A61M 1/3627; A61M 1/3639; A61M 1/3643; A61M 1/3644;
(Continued)

(56) References Cited

U.S. PATENT DOCUMENTS

| 8,142,384 B2 | 3/2012 | Becker |
| 2009/0036816 A1 | 2/2009 | Becker |

(Continued)

FOREIGN PATENT DOCUMENTS

| EP | 2 883 558 | 6/2015 |
| GB | 1 527 380 | 10/1978 |

(Continued)

OTHER PUBLICATIONS

Article, Macdougall, I.C. et al., "Improving the response to ESA therapy in Haemodialysis Patients", poster SAT445 at the World Congress of Nephrology, Cape Town, Mar. 13-17, 2015 Available online at: http://www.posters2view.eu/wcn2015/view.php?nu=3109.

(Continued)

*Primary Examiner* — John Kim
(74) *Attorney, Agent, or Firm* — Brinks Gilson & Lione; John C. Freeman

(57) ABSTRACT

A dialysis bloodline set includes an arterial chamber with upper, lower and central portions, in which the central portion forms a vertical riser tube having a maximum section area less than that of the lower portion. The lower portion has a shoulder which is positioned to deflect blood entering the lower portion to flow across the aperture at the lower end of the riser tube. The bloodline is prepared by filling the arterial chamber with a priming liquid which extends to a level part way up the riser tube and which is partially displaced by the blood to leave a plug of priming liquid within the base of the riser tube above the blood. The plug of priming liquid separates the blood from a gas in the upper part of the arterial chamber while the blood flowing across the aperture forms a dynamic interface.

18 Claims, 9 Drawing Sheets

(52) U.S. Cl.
CPC ........ *A61M 1/3639* (2013.01); *A61M 1/3643* (2013.01); *A61M 1/3644* (2014.02); *A61M 1/3646* (2014.02); *A61M 2205/3344* (2013.01)

(58) Field of Classification Search
CPC .............. A61M 1/3646; A61M 1/3652; A61M 2205/3344
See application file for complete search history.

(56) References Cited

U.S. PATENT DOCUMENTS

| | | |
|---|---|---|
| 2009/0071911 A1 | 3/2009 | Folden |
| 2009/0099498 A1 | 4/2009 | Demers |
| 2011/0108474 A1 | 5/2011 | Folden |

FOREIGN PATENT DOCUMENTS

| | | |
|---|---|---|
| WO | WO 03/055543 | 7/2003 |
| WO | WO 2007/050211 | 5/2007 |
| WO | WO 2013/138233 | 9/2013 |

OTHER PUBLICATIONS

Search Report dated Oct. 22, 2015 from related Great Britain priority Application No. 1507540.1 (5 pages).
Search Report dated Dec. 8, 2015 (1 page) from Great Britain priority Application No. GB1509911.2.
International Search Report dated Aug. 2, 2016 (2 pages) from PCT priority Application No. PCT/GB2016/051660.
Written Opinion of the International Searching Authority dated Aug. 2, 2016 (10 pages) from PCT priority Application No. PCT/GB2016/051660.
Non-Final Rejection dated Sep. 28, 2017 (10 pages) from related U.S. Application No. 15/143,980.

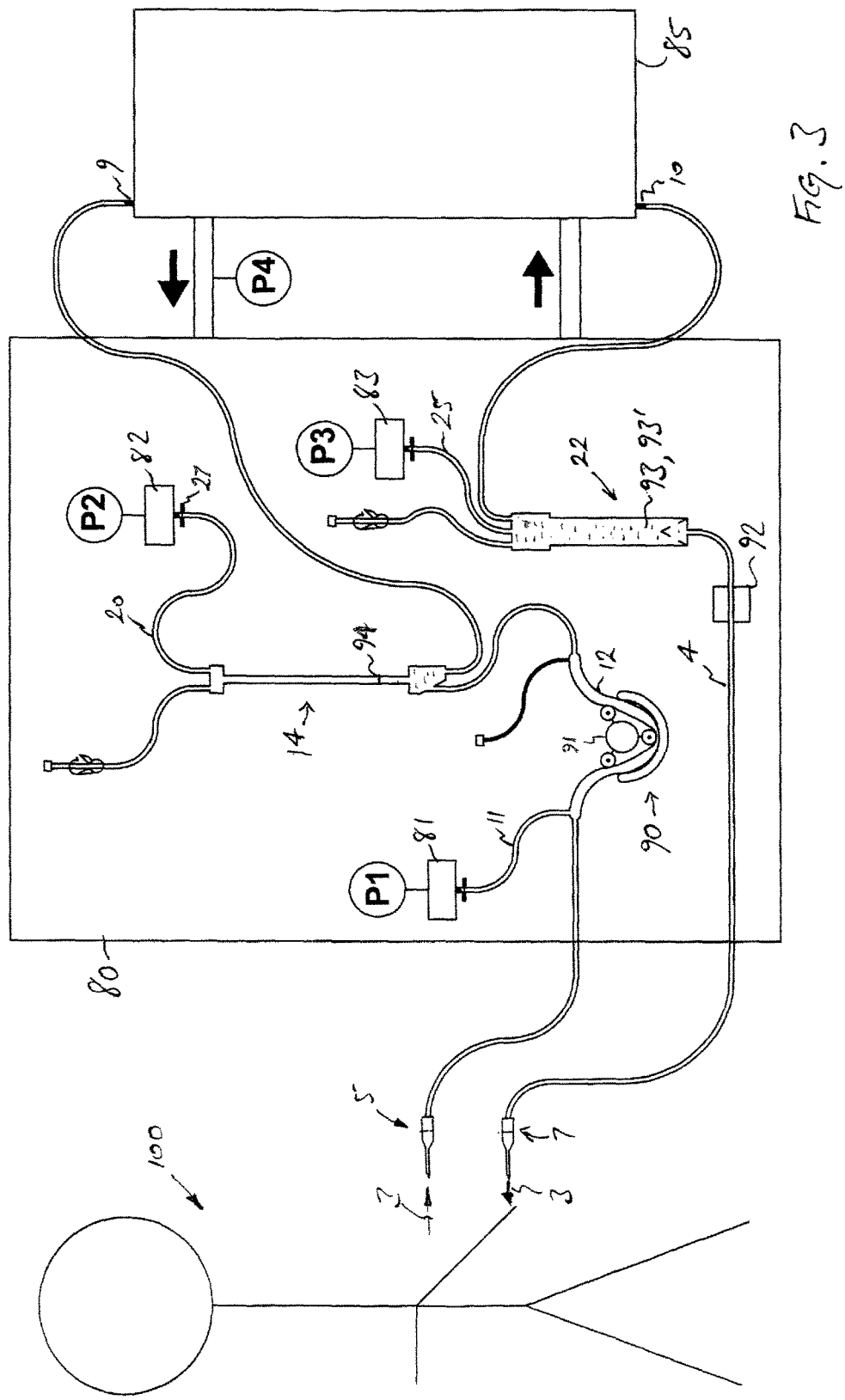

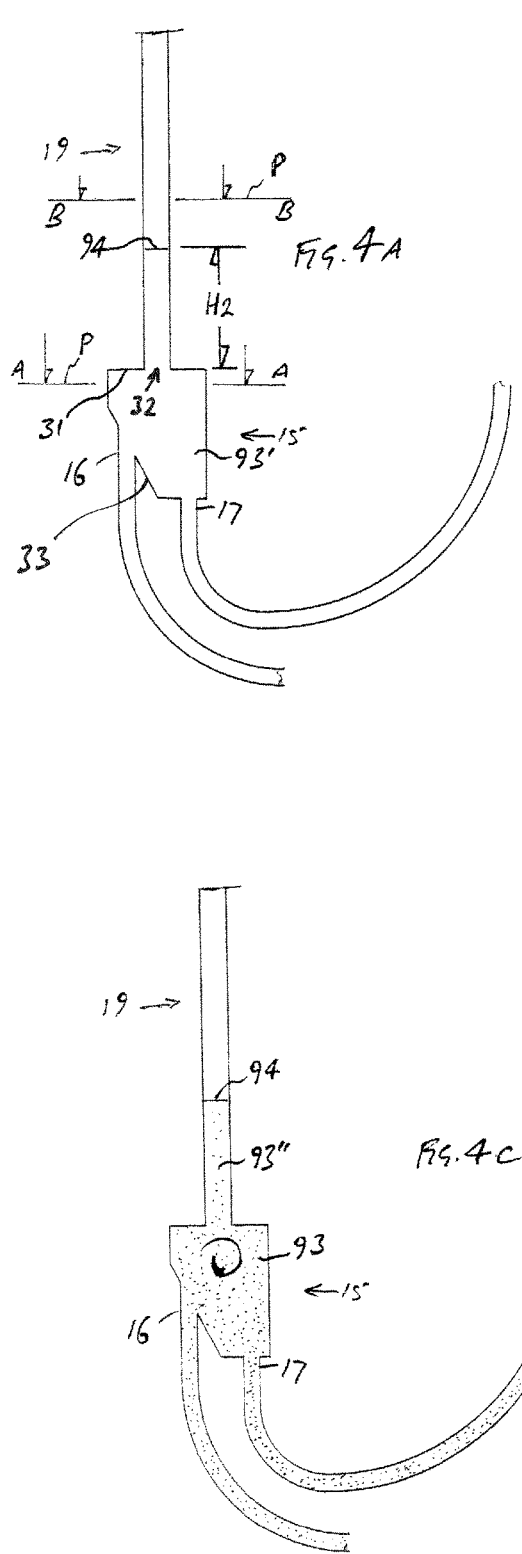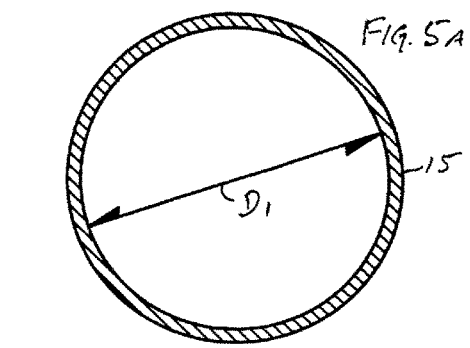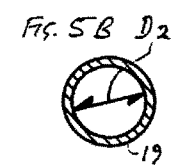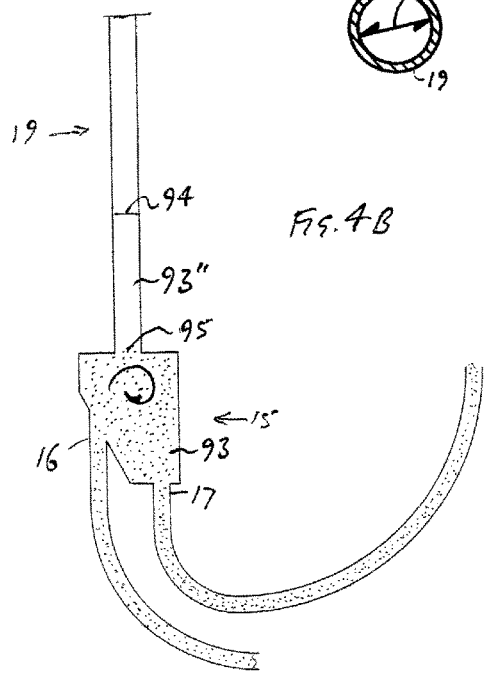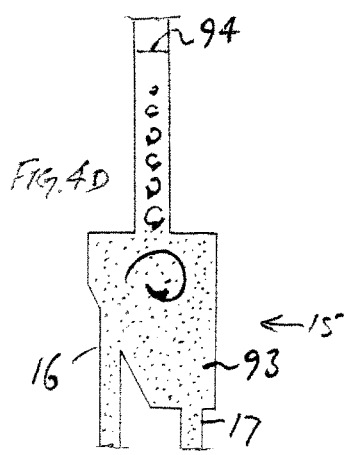

DIALYSIS BLOODLINE SET AND METHOD OF USE

This application claims priority to International Application No. PCT/GB2016/051660 filed Jun. 6, 2016 and to Great Britain Application No. 1509911.2 filed Jun. 8, 2015; the entire contents of each are incorporated herein by reference.

This invention relates to bloodline sets for conveying a patient's blood to and from a dialyzer.

In this specification, the term "dialysis" is taken to include haemodialysis, haemofiltration and haemodiafiltration, and the term "dialyzer" is construed mutatis mutandis to include a haemofilter.

The dialysis procedure requires three principal components: a dialyzer, a bloodline set (hereinafter referred to simply as a bloodline) comprising one or more tubing assemblies and associated components for connecting the dialyzer to the patient, and a dialysis machine for controlling the flow of blood and (in haemodialysis and haemodiafiltration) also the dialysate through the bloodline and the dialyzer.

A dialyzer comprises a semi-permeable membrane which separates blood from a dialysate or, in the case of haemofiltration, a filtrate compartment. Typically the membrane comprises a bundle of straws, each straw defining a lumen through which the blood flows. The dialyzer may be discarded after a single use or cleaned and re-used multiple times for the same patient.

The dialysis machine monitors and maintains at an optimal setting the transmembrane pressure (the difference in pressure between the blood on one side of the membrane and the dialysate or filtrate compartment on the other) and the speed of the pump which urges the blood through the bloodline and the dialyzer and back to the patient, responsive to the inputs from a number of fluid pressure sensors which are fluidly connected to the bloodflow through the bloodline via air filled tubes.

Typically the bloodline is the simplest and least expensive part of the apparatus and is discarded after a single use.

The bloodline incorporates an arterial chamber and a venous chamber arranged respectively before and after the dialyzer in the direction of flow. In use, the blood flows through a lower portion of the arterial chamber so that a blood/air interface is formed in a central portion of the chamber above the lower portion.

The arterial chamber provides a cushion of air above the interface, sufficient to decouple the dialyzer and other downstream components from the pressure pulses from the peristaltic pump. The blood/air interface provides an immediate visual indication of the pulsatile flow condition, reflecting the operation of the pump, and also transmits fluid pressure via an air filled pressure sensing line to a pressure sensing port on the dialysis machine which is arranged to adjust or stop the pump in the event of an abnormal pressure condition.

Disadvantageously, contact between blood and air at the blood/air interface activates the clotting cascade and so causes damage to the red blood cells. U.S. Pat. No. 8,142,384 teaches a bloodline in which the internal section area of the central portion of the arterial chamber is reduced to ⅐ of that of the lower portion, whereby blood/air contact is substantially reduced so that less damage occurs to the red blood cells and the requirement for EPO, heparin and other drugs is concomitantly reduced. It is also known from U.S. Pat. No. 8,142,384 that the venous chamber may be completely filled with blood, although in clinical practice it is normal for the upper part of the venous chamber also to be filled with air. The blood drips through the air pocket so that any air bubbles entrained in the bloodflow returning from the dialyzer are retained in the venous chamber.

In another approach, it is known to mask the blood/air interface in the arterial chamber with a layer of another fluid, although this is seldom done in practice due to the complexity it introduces into the procedure. Where the masking fluid is miscible with blood, it may become entrained in the blood flow, particularly where the contact area between the fluids is in motion. The masking fluid may therefore be arranged to stagnate so as to reduce undesirable mixing and entrainment of the masking fluid into the blood flow. However, this in turn can result in a stagnant layer of blood immediately beneath the blood/fluid interface, which is equally undesirable.

It is also known to provide a microporous membrane to separate blood from air; however, it is found that the membrane can become blocked in use by proteins deposited from the blood.

US2011108474 (A1) discloses an airless chamber with a microporous membrane for removing air bubbles entrained in the blood flow and a layer of saline which separates the membrane from the blood flowing through the larger, lower region of the chamber to reduce fouling of the membrane.

If the arterial chamber in a dialysis bloodline does not provide an air cushion defining a liquid/air interface, then the bloodline must be further adapted to incorporate expandable wall portions or other special features for accommodating transient pressure and volume changes upstream of the dialyzer and actuating the pressure sensing system of the dialysis machine which is adapted to receive it. An airless arterial chamber therefore will not be compatible with many dialysis machines which are arranged to sense the fluid pressure between the pump and the dialyzer via a pressure sensing line communicating with an air cushion in the arterial chamber.

The general object of the present invention is to provide a dialysis bloodline of the type in which the arterial chamber provides a cushion of air or other gas in fluid communication with a pressure sensing line to the dialysis machine while contact with air giving rise to damage to red blood cells is reduced.

Accordingly the invention provides a bloodline set and a method as defined in the claims.

Further more specific objectives, features and advantages will be evident from the illustrative embodiments of the invention which will now be described, purely by way of example and without limitation to the scope of the claims, and with reference to the accompanying drawings, in which:

BRIEF DESCRIPTION OF THE DRAWINGS

FIG. 3 shows the novel bloodline in use on the dialysis machine;

FIGS. 4A, 4B and 4C show the first arterial chamber of the novel bloodline, respectively when primed with saline solution during preparation of the dialysis machine (FIG. 4A); at the beginning of the dialysis session (FIG. 4B); and part way through the dialysis session (FIG. 4C);

FIG. 4D is an enlarged view of part of the first arterial chamber in use; and FIGS. 5A and 5B are sections respectively at line A-A and line B-B in a plane P normal to the vertical axis of the first arterial chamber in the use position as shown in FIG. 4A;

Figure 1:
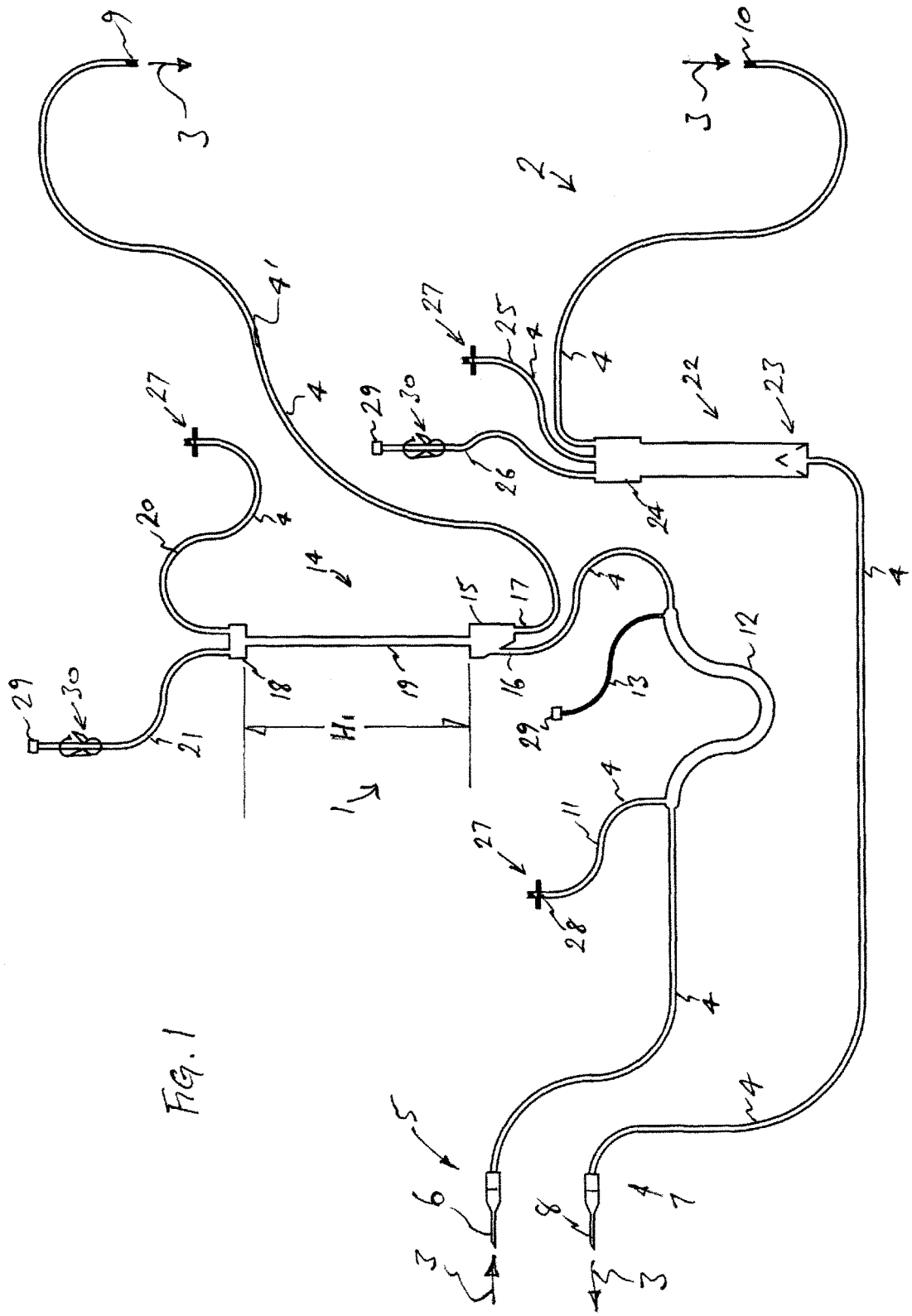
FIG. 1 shows a disposable bloodline including a first arterial chamber in accordance with a first embodiment of the invention.

Reference numerals appearing in more than one of the figures indicate the same or corresponding features in each of them.

Referring to FIG. 1, a bloodline comprises first and second sterile tubing assemblies 1, 2 made from flexible plastics material as known in the art and defining a flowpath 3 through a bore 4' of the tubing 4 and other components of the bloodline for conveying blood to and from a patient via a dialyzer. The first tubing assembly 1 includes a patient inflow end 5 having a connector for fluidly connecting the tubing to a needle 6 which is inserted into a suitable access point (e.g. an arteriovenous fistula or catheter) to receive a flow of blood from the patient 100. The second tubing assembly 2 similarly has a patient outflow end 7 having a connector for fluidly connecting the tubing to a needle 8 for returning the flow of blood to the patient. In the illustrated example the inflow and outflow ends are separate but they could be combined into a single assembly as known in the art.

The first tubing assembly terminates in a dialyzer inlet connection 9 for connection to the inlet of a dialyzer, and the second tubing assembly terminates similarly in a dialyzer outlet connection 10 for connection to the outlet of the dialyzer. A plurality of auxiliary lines comprising pressure sensing lines, pressure balancing or vent lines, and injection lines are also fluidly connected to the flowpath 3 at various points along the bloodline. Many of these auxiliary lines are adapted for more than one function, for example, to vent air or other gas from the bloodline and to provide an injection port through which drugs can be injected into the bloodflow, as known in the art.

Between the inflow end 5 and the dialyzer inlet connection 9, the first tubing assembly includes a first pressure sensing line 11, an enlarged bore elastomeric silicone tubing section 12 to fit the peristaltic pump of the dialysis machine, a heparin injection line 13, and a first arterial chamber 14.

In the use position as shown in FIG. 3, the arterial chamber 14 comprises a lower portion 15, an upper portion 18, and a central portion 19 forming a vertical riser tube (i.e. a riser tube having a vertical length axis) which is arranged between the lower portion and the upper portion. In this specification, the term "central portion" 19 should be construed to mean simply: that portion which is arranged between the lower portion and the upper portion, and is not intended to imply any more particular dimensional or geometric relationship of centrality or symmetry between the respective parts. The lower portion includes an arterial chamber inflow connection 16 and an arterial chamber outflow connection 17 so that in use the flowpath extends through the lower portion between the inflow and outflow connections and the blood circulates within the lower portion between them. Preferably at least the central portion 19 and, more preferably, the whole of the arterial chamber 14 is transparent so that the level of the liquid/gas interface in the central portion can be observed by the clinical technician in use.

In the illustrated example the upper portion 18 has an enlarged section area relative to the central portion 19 so as to form a gas reservoir which also functions as a manifold at the upper end of the riser tube. Two auxiliary lines comprising a second pressure sensing line 20 and an injection or pressure balancing line 21, also referred to as a vent line, are connected to the upper manifold portion 18 as shown in fluid communication with the lower portion and inflow and outflow connections. In alternative embodiments the pressure balancing line 21 could be absent, or additional auxiliary lines could be provided. In further alternative embodiments the upper manifold portion 18 could have a section area similar to that of the central portion 19.

Between the dialyzer outlet connection 10 and the patient outflow end 7 the second tubing assembly includes a venous chamber 22, which may have a filter at its lower outlet end 23 as shown. The upper inlet end 24 comprises a manifold to which are connected a third pressure sensing line 25 and an injection line 26.

Each of the pressure sensing lines terminates at a connector 27 with a gas permeable membrane 28, which is arranged to prevent the flow of blood in the exceptional event that blood should travel along the pressure sensing line to the connector 27, while transmitting pressure via the column of gas trapped in the tubing 4 of the pressure sensing line through the membrane to a pressure sensor of the dialysis machine which is in fluid communication with the blood flow via the gas column and the liquid/gas interface in the arterial chamber as further explained below.

Each of the injection lines terminates at a removable cap 29 so that it can be used to introduce medication or other fluid into the blood during dialysis, or in the case of the injection line 21, to control the flow of gas to and from the arterial chamber so as to regulate the level of blood in the riser tube. Depending on the type of dialysis machine, this function may also be performed automatically via the pressure sensing line 20.

Elastic plastics clamps 30 are also provided on various ones of the lines, each clamp being moveable between a locked position and an open position. In the locked position the clamp compresses the tubing 4 so that the bore 4' is closed to prevent flow past that point. In the open position the bore 4' is unobstructed.

The bloodline need not include all the illustrated components, but will typically include other components in addition to those illustrated. For example, a bag for collecting a priming liquid (typically a saline solution) may be releasably connected to the patient outflow end 7, with the tubing at that end being closeable by another clamp 30 so that after priming the bloodline with the saline solution or other priming liquid, and then displacing the saline solution as blood flows from the patient towards the patient outflow end 7, the patient outflow end can be sealed with the clamp 30 before disconnecting the bag of used saline solution, and then re-connected to the patient before releasing the clamp to allow blood to circulate through the dialyzer and back to the patient. Other conventional features will be familiar to those skilled in the art and are not described here in detail.

Figure 2:
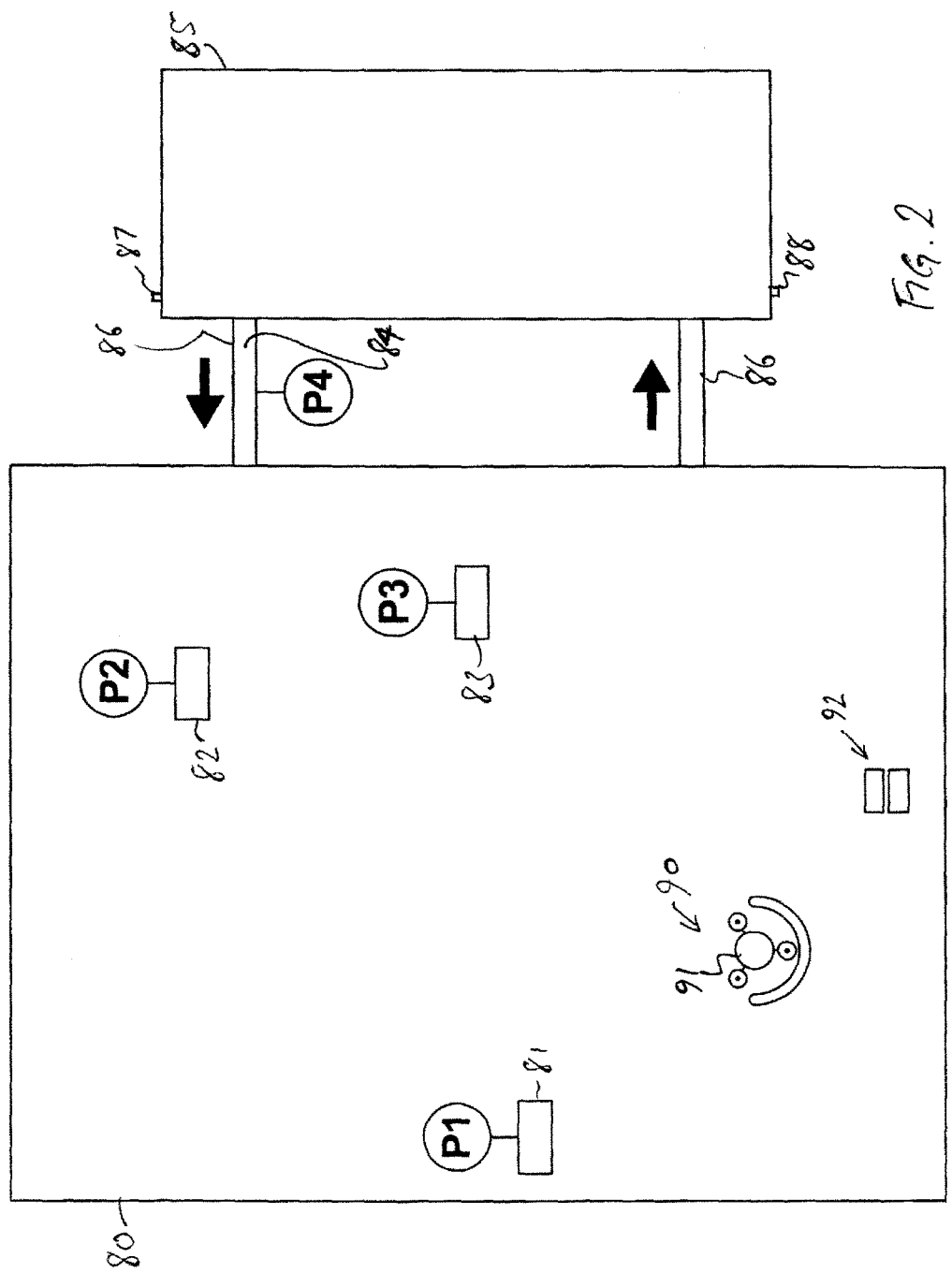
FIG. 2 shows a dialysis machine.
Figure 6B:
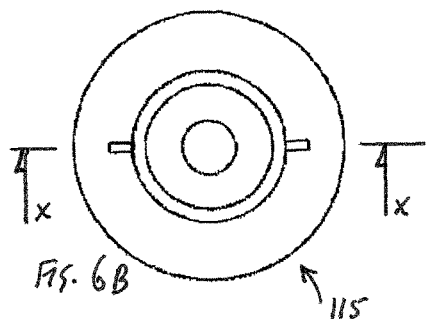
FIGS. 6B and 6C are respectively a top view and a bottom view of the lower portion of the second arterial chamber with the riser tube and inlet and outlet tubes removed.
Figure 6A:
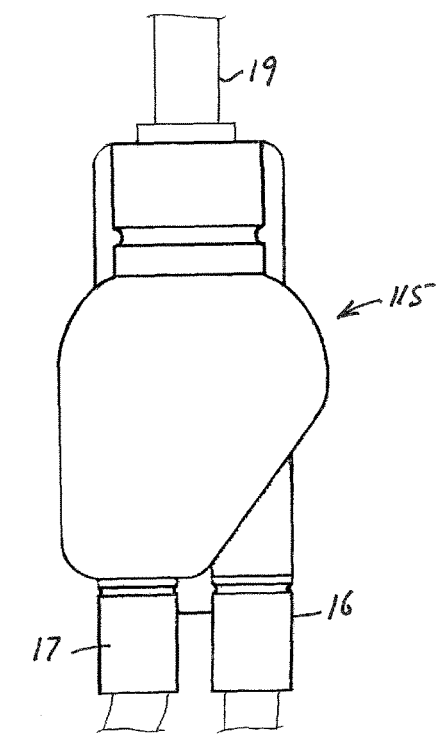
FIG. 6A shows the lower portion and part of the central portion of a second arterial chamber.
Figure 6C:
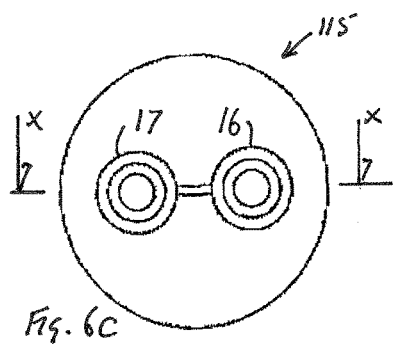
Figure 7:
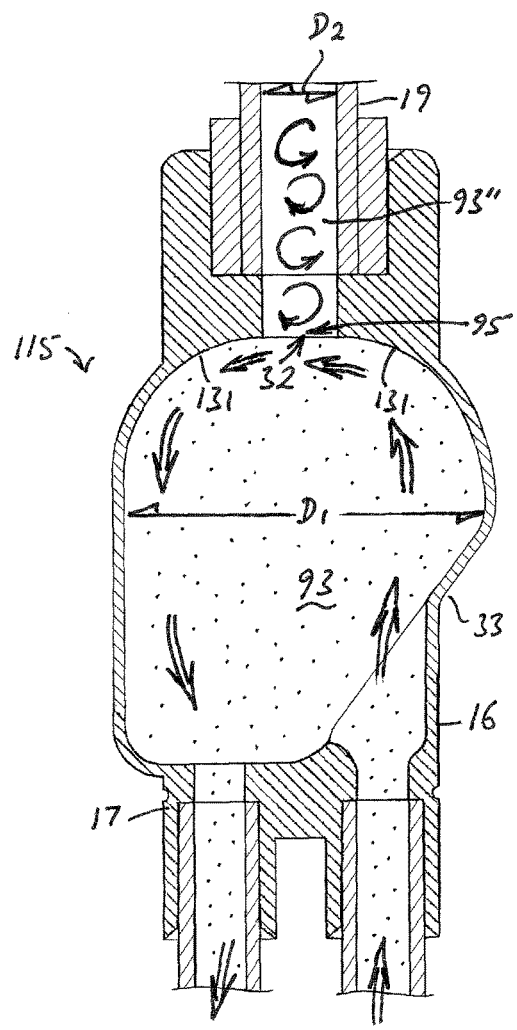
FIG. 7 is a longitudinal section taken in a vertical plane at X-X through the centre of the second arterial chamber.

Referring to FIG. 2, the example dialysis machine 80 includes three pressure sensors having respective pressure sensing ports 81, 82, 83 for connection to the three connectors of the bloodline pressure sensing lines 11, 20, and 25 respectively. The fluid connection between each pressure sensing line and its point of connection with the blood flowing through the tubing 4 allows the dialysis machine to sense the fluid pressure P1, P2, P3 at each of those points. A peristaltic pump assembly 90 driven by a motor 91 is arranged to receive the tubing section 12 of the bloodline, and a bubble sensor 92 is arranged to receive the tubing 4 at the outlet end 23 of the venous chamber so as to sense any gas (usually air) entrained in the blood flow at that point.

The dialysis machine is connected via dialysate flowpaths 86 to a dialyzer 85 through which it pumps the dialysate 84 in the direction indicated by the arrows. A fourth internal pressure sensor detects the fluid pressure P4 of the dialysate 84 in the dialyzer 85 or (where the dialyzer is a haemofilter) the pressure within the filtrate chamber. The dialyzer also has inlet 87 and outlet 88 connections for the bloodline.

Referring to FIG. 3, the bloodline is connected to the dialysis machine and to the dialyzer with the patient inflow and outflow ends connected to a suitable access point on the patient so that blood 93 can circulate from the patient via the dialyzer inlet and outlet connections 9, 10 which are connected to the inlet and outlet of the dialyzer so that the flowpath 3 passes through the dialyzer and back to the patient. The connectors 27 of the pressure sensing lines are connected to the respective pressure sensing ports of the dialysis machine which controls the motor 91 of the pump. Since there is no barrier to liquid between the inflow and outflow connections 16 and 17 and the pressure sensing line 20, any changes in blood flow or pressure will alter the level of the liquid/gas interface in the riser tube and cause a pressure change in the pressure sensing line 20. The pressure sensing line 20 thus places the respective pressure sensor of the dialysis machine in fluid communication via the gas cushion in the arterial chamber with the blood flow between the pump and the dialyzer, so that it can react to abnormal pressure conditions resulting for example from blockage of the dialyzer.

Referring also to FIG. 4 and FIGS. 5A and 5B, each portion of the arterial chamber has a maximum internal section area defined in a horizontal plane P in the use position. The central portion 19 has a maximum internal section area less than that of the lower portion 15. In the example shown, the upper and central portions and the largest, upper part of the lower portion 15 are generally cylindrical and so their maximum internal diameters respectively define their maximum internal section areas, represented by diameter D1 for the lower portion 15 and diameter D2 for the central portion 19. The lower part of the lower portion 15 comprises an inclined base wall 33 as shown which encourages the desired circulatory flowpath within the lower chamber. Preferably the inflow connection 16 is higher than the outflow connection 17 in the use position, as shown, although other configurations are possible. In other embodiments the portions may have other tubular shapes, and their section area may also vary along the length axis of the arterial chamber.

Preferably the central portion has a maximum internal section area not more than 50%, more preferably not more than 25%, most preferably not more than 15% of that of the lower portion, which provides adequate volume in the central portion to enable the user to conveniently adjust the height of the liquid column while minimising the area of the liquid/gas interface 94 which is positioned in the central portion as further explained below.

The lower portion 15 includes a shoulder 31 which in the illustrated example is an annular horizontal surface defining an aperture 32 at which the central portion is fluidly connected to the lower portion. In use, the shoulder deflects the blood 93 circulating in the lower portion of the arterial chamber, and may form a discernible eddy in the lower portion as shown by the circulating arrow in FIGS. 4B and 4C. The internal section area of the arterial chamber at the shoulder 31 is reduced relative to the internal section area immediately below it in the use position.

Preferably the shoulder is located at the position where the lower portion 15 is connected to the central portion 19, so that after priming the bloodline, when blood is introduced into the lower portion to displace the priming liquid while maintaining a constant amount of gas in the upper part of the arterial chamber, the blood forms an interface with the residual plug of priming liquid at or proximate the same position as the shoulder. This in turns means that the interface will then form the dynamic boundary between the blood deflected by the shoulder to flow across the aperture 32 through the lower portion of the chamber and the relatively stagnant plug of priming liquid above the aperture, as further explained below.

In the example shown, the shoulder defines the upper extremity of the lower portion and forms the transition from the lower portion to the central portion. It will be understood that in FIGS. 4A-4C the wall thickness of the illustrated components, shown in FIGS. 5A and 5B, is ignored so that FIGS. 4A-4C represent the internal surfaces of the arterial chamber and its associated flowpaths. In practice, the transition from the shoulder to the central portion and/or to the larger part of the lower portion (in the illustrated example, to the cylindrical internal wall (visible in FIG. 5A) of the largest, upper part of the lower portion) may be rounded, and the shoulder could be curved or angled rather than normal relative to the vertical axis of the arterial chamber in the use position as shown. Less preferably, the shoulder could be arranged somewhat below the transition from the lower portion to the central portion.

In use, the dialysis machine and dialyzer are prepared for dialysis by connecting the bloodline to the dialysis machine and the dialyzer and priming the bloodline by filling the flowpath with a priming liquid 93', typically a saline solution, so that in a primed condition the priming liquid 93' fills the lower portion and part of the central portion of the arterial chamber, as shown in FIG. 4A. This can be achieved by tilting the arterial chamber and/or venting gas from the injection line 21 or (where the dialysis machine so allows) by adjusting the pressure in the pressure sensing line 20, as the priming liquid flows through the bloodline.

After priming the bloodline with the priming liquid, the bloodline is connected to the patient and blood is introduced into the flowpath to displace the priming liquid and fill the lower portion of the arterial chamber. Due to the reduced section area of the central portion 19, the blood circulates through the lower portion 15 but not through the central portion 19 so that a plug 93" (i.e. an isolated body) of priming liquid is left in the central portion above the blood, as shown in FIG. 4B.

During the admission of blood to displace the priming liquid in the lower portion of the arterial chamber, the liquid/gas interface 94 is preferably maintained at approximately a constant level, so that the body of priming liquid within the central portion 19 is isolated to form the plug 93". This can be achieved by maintaining a constant quantity of gas in the upper part of the arterial chamber while introducing the blood, i.e. gas is neither admitted nor permitted to flow out of the upper portion of the arterial chamber, or by maintaining or adjusting the gas pressure to maintain the liquid/gas interface 94 at a desired level within the central portion.

The procedure described represents a departure from the conventional procedure for preparing a dialysis bloodline, in which the priming liquid is introduced to such a level that when the bloodline is connected to the patient, the blood substantially completely displaces the priming liquid from the arterial chamber, with the level of the blood being subsequently adjusted and, typically, allowed to rise some way up the arterial chamber when the pump begins to generate flow resistance through the dialyzer, so as to define a blood/gas interface part way up the height of the arterial chamber.

After introducing blood into the flowpath to form a plug 93" of priming liquid as described, the blood is then circulated by the pump through the flowpath. As the blood flows through the lower portion of the arterial chamber it is deflected by the shoulder 31 and may form a discernible eddy in the lower portion of the arterial chamber beneath the plug 93" of priming liquid. In use it is found that a well-defined interface 95 is initially formed between the circulating blood and the plug 93" of priming liquid at the base of the central portion 19 of the arterial chamber, with the blood immediately below the interface 95 remaining continuously in motion so that it does not stagnate (FIG. 4B). In the illustrated example, where the maximum internal section area of the central portion is about 15% of that of the lower portion, it is found that this interface persists for the duration of a 4 hour dialysis session, during which time blood slowly diffuses into the plug 93" of priming liquid so that the plug of priming liquid very slowly takes on a red colouration and after about half an hour resembles a glass of red Burgundy wine (FIG. 4C). After about four hours, at the end of the dialysis session, the colour of the plug of priming liquid is still visibly distinguishable on close inspection from the blood in the lower part of the arterial chamber.

It is found in practice that in combination, the reduced section area of the central portion 19 of the arterial chamber together with the dynamic interface 95 between the blood flow deflected by the shoulder 31 and the plug 93" of priming liquid in the central portion 19 above it maintains all of the blood in motion while separating the blood from the volume of air or other gas contained in the upper part of the arterial chamber so effectively that damage to red blood cells due to contact with air and the concomitant requirement for added EPO are greatly reduced, even in comparison with a bloodline having an arterial chamber with a reduced diameter portion in which a blood/air interface is formed in use in the conventional way.

Moreover, it is believed that the rate at which blood infuses into the plug 93" of priming liquid is much slower than would be the case for example in an arterial chamber having a central portion of equal or similar section area to the lower portion and a layer of special masking liquid on top of the blood, due to the dynamic interface 95 between the blood flowing through the larger, lower portion and the plug of priming liquid which is located in the substantially smaller, central portion 19 above it. This dynamic interface 95 forms a boundary or shear plane characterised by the difference in velocity between the relatively faster and more energetic blood flow below the interface compared with the comparatively stagnant or much more slowly moving plug of priming liquid in the lower part of the central portion above the interface. The dynamic interface 95 effectively separates the blood from the less dense priming liquid, which excludes air or other gas from the blood, while allowing the blood to remain continuously in motion so that the blood is maintained in optimal condition for the duration of the dialysis session.

Moreover, where the central portion is of small internal diameter or maximum horizontal dimension, particularly not more than about 12 mm internal diameter or maximum horizontal dimension, and the saline plug extends for a greater vertical distance (particularly twice the distance or more) up the central portion or riser tube relative to the internal diameter or maximum horizontal dimension of the central portion, it is found that a stacked series of counter-rotating eddies will be formed above the dynamic interface 95 within the plug of saline or other priming solution, as shown in FIG. 4D. The eddies weaken progressively towards the liquid/gas interface and effectively stratify the plug of priming solution into distinct circulating bodies so that the dynamic interface 95 is characterised by little mixing of the two liquids, further reducing oxygen transport.

In practice it is found that the separation of blood from priming liquid by the dynamic interface 95 is good enough to allow an ordinary priming liquid such as saline solution to function as an effective barrier to blood/gas contact for the duration of the dialysis session, even though it may be perfectly miscible with blood and of very similar density.

The novel bloodline may be supplied with instructions, e.g. by way of indicia, e.g. in writing or in symbolic form, or in electronic form, e.g. on a data carrier, or delivered via training to the clinical personnel who are to use it, whereby the user is directed, after connecting the bloodline set to the dialysis machine and to the dialyzer, to fill the flowpath with the priming liquid to establish the primed condition wherein the priming liquid fills the lower portion and a lower part of the central portion 19 of the arterial chamber to the required level.

Preferably the priming liquid 93' extends up the central portion 19 of the arterial chamber to define a liquid/gas interface 94 at a level between 5% and 90%, more preferably 10% and 50%, most preferably 15% and 30% of a vertical height H1 of the central portion in the use position. The level of the liquid/gas interface 94 is indicated in FIG. 4A by its height H2 as a proportion of the total vertical height H1 of the central portion 19. The upper portion 18 and the upper part of the riser tube formed by the central portion 19 above the liquid/gas contact interface 94 are filled with gas. It will be understood that the gas will typically be air, since the bloodline will most conveniently be full of air when it is manufactured and stored before use. References herein to gas, gas pressure, a gas column, a liquid/gas interface and so forth may therefore be construed in a typical use situation as references to air, air pressure, an air column and a liquid/air interface etc. Of course, if desired, the bloodline or specific gas-containing regions of the bloodline may be filled before or in use with a gas other than air.

Optionally, the instructions may direct the user when priming the bloodline to fill the venous chamber substantially completely with the priming liquid 93' as shown in FIG. 3, conveniently by tilting the venous chamber and/or venting gas from the vent line 26 as the priming liquid flows through the bloodline. The venous chamber can then be substantially completely filled with blood 93 as the blood flows through the bloodline and displaces the priming liquid at the beginning of the dialysis session, as also shown in FIG. 3, which removes the blood/air interface conventionally present in the venous chamber and so further reduces damage to the red blood cells due to contact with air. The venous chamber could also be substantially completely filled with blood after partially filling it with the priming solution.

Of course, if preferred, the venous chamber may be only partially filled with priming liquid and subsequently with blood in accordance with conventional practice. In practice it is found that during a four hour dialysis treatment session, and particularly in inflamed patients, the red blood cells tend to separate from the plasma as the blood pools in the venous chamber, forming a floating layer of plasma in the venous chamber which helps to reduce damage to the red blood cells within the venous chamber by reducing contact with air.

FIGS. 6A-6C and 7 show the lower portion 115 of a second arterial chamber, which is a plastics moulding generally similar to the lower portion 15 of the first arterial chamber. The second arterial chamber has a central portion 19 and upper portion 18 as described above and may be incorporated into the bloodline in place of the first arterial chamber and primed and used in the same manner. The features of the second arterial chamber generally correspond to those of the first, and the optional features and variants described with reference to the first arterial chamber may be equally applied to the second. Preferably, as with the first arterial chamber, the central portion 19 has a maximum internal section area D2 not more than 50%, more preferably not more than 25%, most preferably not more than 15% of that of the lower portion 115, defined by its maximum diameter D1 in a horizontal plane normal to the central axis of the riser tube in its use position.

As in the first arterial chamber, the lower portion of the chamber is bounded by an inclined base wall 33 which slopes downwardly in the use position from the inflow connection towards the outflow connection, and the inflow connection opens into the lower portion through the inclined base wall.

The lower portion 115 of the second arterial chamber includes a rounded shoulder 131 on each of the inflow and outflow sides of the aperture 32 at which the reduced diameter central portion 19 opens into the lower portion 115, the shoulders forming respective portions of an annular upper wall of the lower portion which surrounds the aperture 32. The shoulder 131 on the inflow side is arranged to deflect the blood flowing into the lower portion from the inflow connection 16 so that it flows generally horizontally across the aperture 32 in a flowpath generally transverse or normal to the vertical central axis of the riser tube, below the priming liquid in the lower part of the central portion, while the shoulder 131 on the outflow side guides the blood flow back down the opposite wall of the lower portion to the outflow connection 17, as indicated by the arrows in FIG. 7.

The blood in the middle of the lower portion remains in very slow motion, and may form a slight eddy similar to that described above with reference to the first chamber, so that air bubbles entrained in the blood entering the chamber can rise towards the plug of priming liquid and, when the blood flow slows between pulses, may enter and rise through the plug of priming liquid to exit at the liquid/gas interface.

A dynamic interface 95 is defined between the plug 93" of priming liquid within the central portion 19 and the stream of blood flowing with each pulse of the pump horizontally or transversely past the aperture 32. Advantageously, the shoulder may be arranged to position the dynamic interface 95 at the aperture 32 as shown, so that in a similar way to that previously described, the dynamic interface gives rise to a stacked series of counter-rotating eddies in the plug of priming liquid 93", indicated by the circulatory arrows in FIG. 7, which progressively decay towards the liquid/gas interface.

The effect is similar to that of the first described chamber, in that the dynamic interface 95 so effectively separates the blood from the priming liquid, e.g. saline solution, that the colour of the blood in the lower chamber is still visibly distinct from that in the plug 93" of priming liquid even at the end of a four hour dialysis session, and the EPO requirement is substantially reduced in comparison with a conventional chamber having a blood/air interface.

Figure 8A:
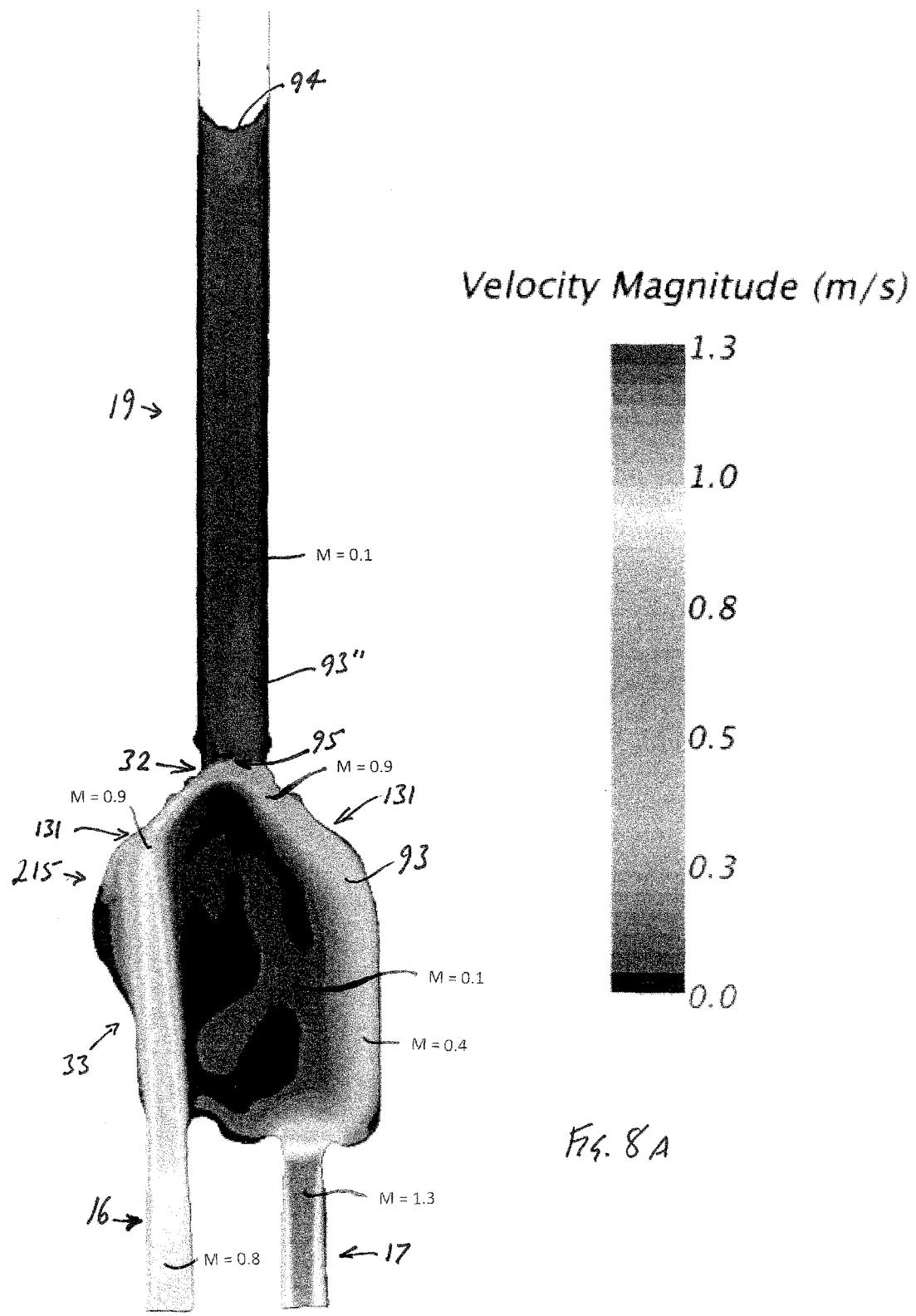
FIGS. 8A and 8B are sections through the interior of a third arterial chamber generally similar to the second arterial chamber and taken in a plane corresponding to that of FIG. 7, showing respectively the peak velocity magnitude and peak vorticity magnitude obtained by CFD simulation of a use condition when incorporated into the disposable bloodline in place of the corresponding parts of the first arterial chamber as shown in FIGS. 4B-4D.
Figure 8B:
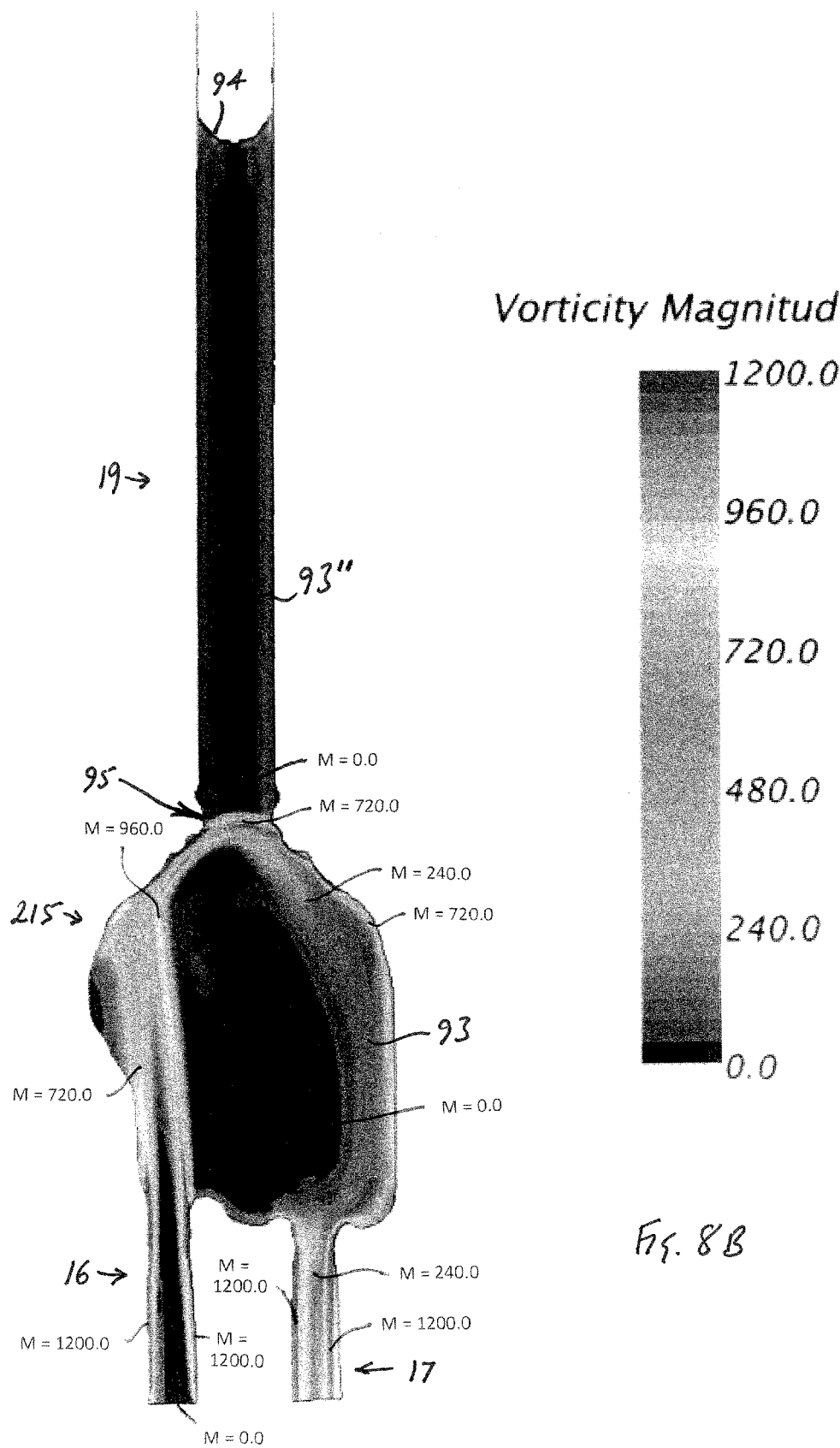
Figure 9A:
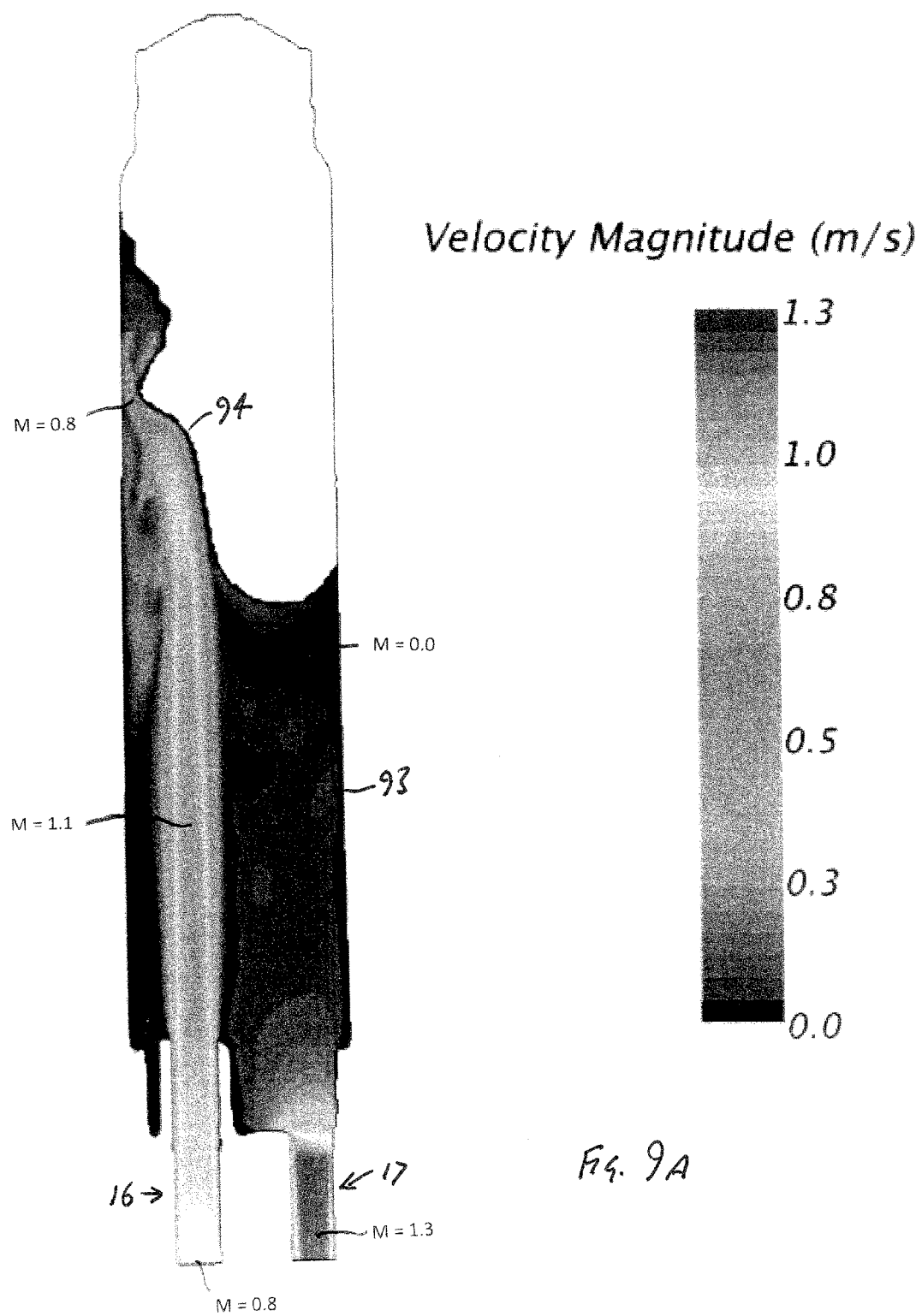
FIGS. 9A and 9B are sections taken in a vertical plane centrally through the interior of a conventional arterial chamber showing respectively the peak velocity magnitude and peak vorticity magnitude obtained by CFD simulation of a use condition by way of comparison with FIGS. 8A and 8B.
Figure 9B:
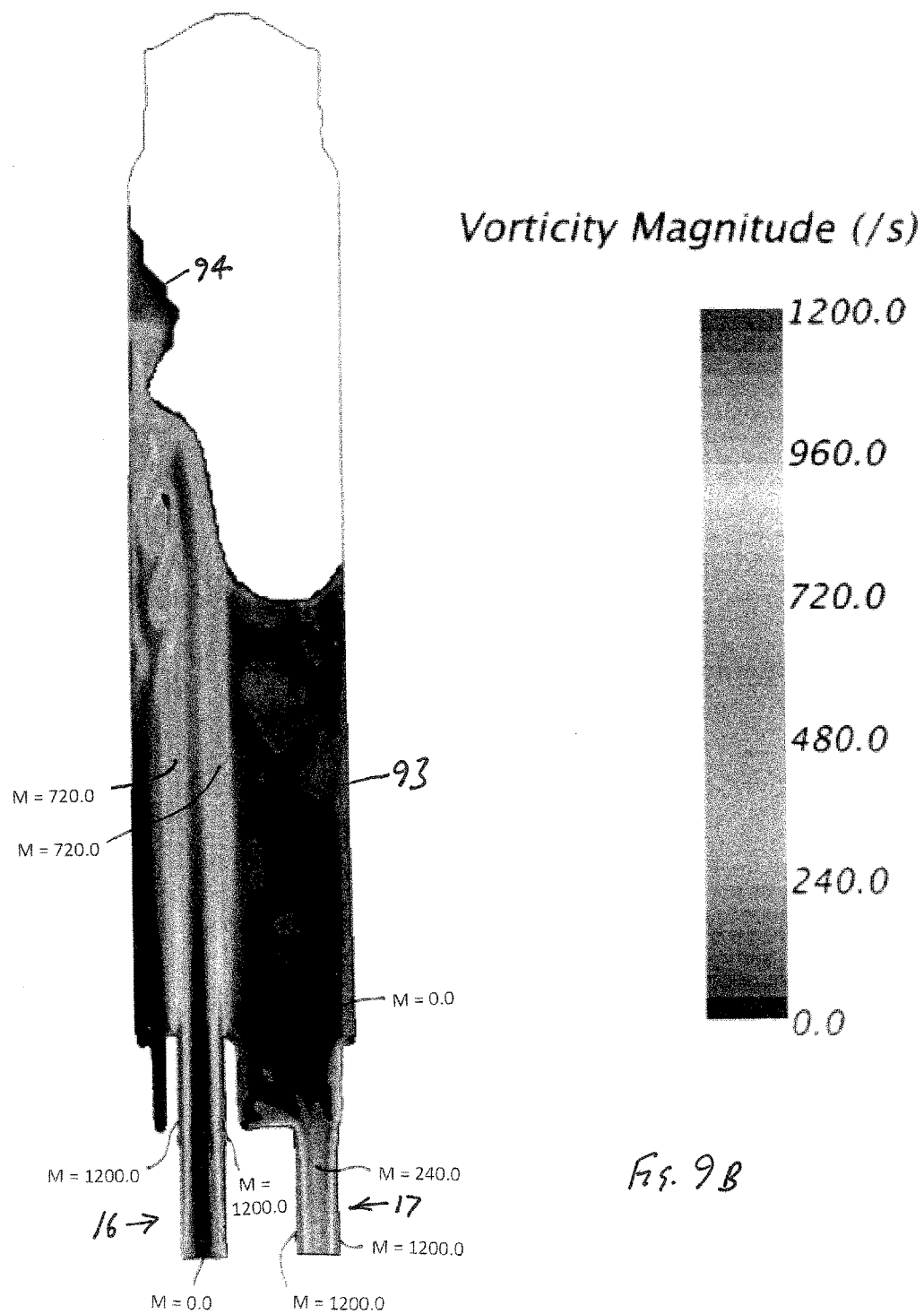

Referring to FIGS. 8A and 8B, a computational fluid dynamics simulation was carried out on a third arterial chamber generally corresponding to the second arterial chamber described above, but in which the lower portion 215 includes deviations from the target geometry of the lower portion 115 resulting from the moulding and assembly processes used during manufacture. A physical chamber was manufactured in accordance with FIGS. 6A-7 and then imaged using a Nikon Metrology HMX ST 225 computer aided tomography scanner to obtain the internal geometry used for the simulation as shown in FIGS. 8A and 8B. Volumetric data was collected in the DICOM format, and the internal surface of each chamber was then extracted as an STL triangulation. Finally, the surface definitions were smoothed and extruded appropriately for use in the simulation.

Temporal variation of the inflow velocity was obtained from 'Pulsatility Produced by the Hemodialysis Roller Pump as Measured by Doppler Ultrasound, Artificial Organs, 2015, D. Fulker et al.' Specifically, a flow measurement taken between the pump and the arterial expansion chamber was used (note that there is a mistake in the paper, and contact was made with the authors to ensure the correct data was used). Data was extracted from the paper via image analysis techniques. Regions of flow reversal were then removed, and the resulting signal was represented using the 10 Fourier modes of greatest amplitude to create a periodic waveform.

CFD simulations in each chamber were undertaken with the following setup:
  Blood Equations—3D time-dependent Newtonian incompressible Navier-Stokes (laminar)
  Air Equations—3D time-dependent compressible ideal gas
  Blood Inflow—Prescribed velocity, time-dependent in accordance with the periodic waveform, uniform in space, with a time-averaged inflow rate of 400 ml/min
  Blood Outflow—Prescribed pressure, fixed in time, uniform in space, chosen to achieve time-averaged inflow pressures of ~220-250 mmHg
  Blood/Air Interface—Volume of Fluid approach
  Wall Boundary Condition—No-slip Simulations were run until all initial transient startup phenomena passed. Subsequently, data was collected and analysed over two full pulse cycles. Grid resolutions were selected in accordance with industry best-practice.

FIGS. 8A, 8B, 9A and 9B show momentary snapshots from the CFD simulation of the blood flow pattern obtained in vertical central planes extracted from the third arterial chamber (FIGS. 8A, 8B) primed as described above to leave a plug 93" of saline solution and in a conventional, straight sided arterial chamber (FIGS. 9A, 9B) when both chambers are supplied with blood by a peristaltic pump at the moment of maximum pulsatile blood inflow. The shading indicates respectively the magnitude of the flow velocity (FIGS. 8A, 9A) and vorticity (FIGS. 8B, 9B), the vorticity being a measure indicative of the degree of local stirring of the blood. The magnitude M of the measured parameter is indicated in each figure at selected points for ease of reference. It can be seen that the flowpath through the lower portion of the third arterial chamber defines a clear dynamic interface 95 at the aperture 32 leaving the liquid/gas interface 94 visibly undisturbed, whereas the prior art arterial chamber demonstrates severe turbulence at the liquid/gas interface 94.

In this simulation, the time-averaged kinetic energy density KE was calculated over two pulse cycles for all liquid in a region above 2 cm below the spatially averaged height of the liquid/gas interface, in a frame of reference moving with the spatially averaged height of the liquid/gas interface, giving a measure of bulk convection in this region. Based on the assumption that convection dominates the transport of oxygen from the blood/air interface to the blood flowing through the arterial chamber, the measure KE can be regarded as a proxy indicator of oxidative damage to the blood. The calculated value KE is not affected by the different liquid/gas contact surface areas of the two chambers.

The calculated value KE was 0.011 mm Hg for the second arterial chamber and 0.20 mm Hg for the conventional chamber. The proxy measurement suggests that the second arterial chamber may be expected to provide a 94% reduction in oxidative damage to the blood as compared with the conventional chamber.

It can be seen from FIGS. 8A and 8B that both velocity and vorticity are very low in the central portion 19, indicating that the stacked eddies which occur in this region circulate slowly with relatively little energy, while a clearly defined dynamic interface 95 is formed in the region of the aperture 32 by the boundary between the relatively static plug 93" of priming liquid in the central portion and the much more energetic flowpath immediately below it.

It will be noted that in the third arterial chamber as shown in FIGS. 8A and 8B, the aperture 32 forms a neck defining in the use position a reduced horizontal section area relative to the lower portion and the central portion. Unexpectedly, it can be seen that although the manufacturing (blow moulding) and assembly process resulted in some departure from the target geometry including local roughness of the internal surfaces of the chamber, the presence of this slight neck or narrowing at the aperture 32 in combination with the generally rounded shoulders 131 appears to prevent any resulting turbulence from agitating the base of the plug 93" of static fluid and is associated with a very marked dynamic interface 95 at the aperture.

In summary, a dialysis bloodline set includes an arterial chamber with upper, lower and central portions, in which the central portion 19 forms a vertical riser tube having a maximum section area less than that of the lower portion 15. The lower portion has a shoulder which is positioned to deflect blood entering the lower portion to flow across the aperture at the lower end of the riser tube. The bloodline is prepared by filling the arterial chamber with a priming liquid which extends to a level part way up the riser tube and which is partially displaced by the blood to leave a plug of priming liquid within the base of the riser tube above the blood. The plug of priming liquid separates the blood from the gas in the upper part of the arterial chamber while the blood flowing across the aperture forms a dynamic interface with the plug of priming liquid. An eddy may be observed in the lower portion, maintaining the blood in constant motion while it diffuses slowly across the interface into the plug of priming liquid over the duration of the dialysis session.

In a development, the bloodline may include a means whereby the priming liquid is caused to rise up the central portion 19 to the correct level. For example, the arterial chamber may be provided with a vent (not shown) which permits gas to escape so that the priming fluid can rise to the required level defined by the position of the vent or cooperating level sensing means, with the vent being closeable manually or by contact of the vent or level sensing means with liquid. Alternatively for example, the upper gas filled part of the arterial chamber may be connected to a bladder (not shown) which is compressed during the priming procedure and then expanded after priming to draw a variable or predetermined volume of gas into the bladder from the upper part of the arterial chamber and so to draw the priming liquid up the central portion to the required level. Priming fluid or gas could also be injected into the arterial chamber, for example, via one of the auxiliary lines to position the liquid/gas interface at the desired level.

In the illustrated embodiment the tubing section 12 which in use is acted upon by the pump assembly is arranged upstream of the arterial chamber 14, so that the pump advantageously provides positive pressure at the arterial chamber. This ensures that the action of the pump does not draw air into the arterial chamber through the auxiliary connections. it will be understood that in alternative embodiments the tubing section 12 could be arranged instead elsewhere in the bloodline set, such as downstream of the arterial chamber 14 between the arterial chamber 14 and the dialyzer 85, in which case the action of the pump may be sensed as a negative rather than positive pressure.

The novel bloodline could include a single tubing assembly or more than two tubing assemblies. Those skilled in the art will appreciate that many other adaptations are possible within the scope of the claims.

The invention claimed is:

1. A bloodline set for conveying blood to and from a patient via a dialyzer, the bloodline set comprising:
    an assembly of tubing defining a flowpath for the blood;
    a patient inflow end for receiving a flow of blood from the patient;
    a patient outflow end for returning the flow of blood to the patient;
    a dialyzer inlet connection and a dialyzer outlet connection for connecting the assembly of tubing respectively to an inlet and an outlet of a dialyzer so that the flowpath passes through the dialyzer;
    an arterial chamber arranged between the patient inflow end and the dialyzer inlet connection;
    a venous chamber arranged between the dialyzer outlet connection and the patient outflow end; and
    a first pressure sensing line;
    the arterial chamber comprising in a use position: a lower portion, an upper portion, and a central portion arranged between the lower portion and the upper portion;
    the first pressure sensing line being fluidly connected to the upper portion of the arterial chamber;
    the lower portion of the arterial chamber comprising a shoulder, an arterial chamber inflow connection and an arterial chamber outflow connection so that the flowpath extends through the lower portion of the arterial chamber between the arterial chamber inflow connection and the arterial chamber outflow connection;
    the lower portion, the upper portion and the central portion of the arterial chamber each having a corresponding maximum internal section area defined in a horizontal plane in the use position;

wherein the maximum internal section area of the lower portion of the arterial chamber is greater than that of the central portion of the arterial chamber; and the bloodline set contains both a gas, which fills the upper portion of the arterial chamber and an upper part of the central portion of the arterial chamber, and a priming liquid which fills the lower portion of the arterial chamber and a lower part of the central portion of the arterial chamber to define a liquid/gas interface in the central portion of the arterial chamber.

2. A bloodline set according to claim 1, wherein the central portion of the arterial chamber opens into the lower portion of the arterial chamber at an aperture, and the shoulder is arranged to deflect blood flowing in use through the lower portion of the arterial chamber from the arterial chamber inflow connection to the arterial chamber outflow connection below the priming liquid in the lower part of the central portion of the arterial chamber to flow across the aperture to form a dynamic interface between the blood from the patient and the priming liquid.

3. A bloodline set according to claim 2, wherein the shoulder is arranged to position the dynamic interface at the aperture so that the blood flowing in use across the aperture induces a stacked series of eddies in the priming liquid in the lower part of the central portion of the arterial chamber.

4. A bloodline set according to claim 1, wherein the venous chamber is substantially completely filled with the priming liquid.

5. A bloodline set according to claim 1, wherein the lower portion of the arterial chamber is bounded by an inclined base wall which slopes downwardly in the use position from the arterial chamber inflow connection towards the arterial chamber outflow connection, and the arterial chamber inflow connection opens into the lower portion of the arterial chamber through the inclined base wall.

6. A bloodline set according to claim 1, wherein the aperture forms a neck defining in the use position a reduced horizontal section area relative to the lower portion of the arterial chamber and the central portion of the arterial chamber.

7. A bloodline set according to claim 1, wherein the central portion of the arterial chamber has a maximum internal section area not more than 50% of that of the lower portion of the arterial chamber.

8. A bloodline set according to claim 1, wherein the central portion of the arterial chamber has a maximum internal section area not more than 25% of that of the lower portion of the arterial chamber.

9. A bloodline set according to claim 1, wherein the central portion of the arterial chamber has a maximum internal section area not more than 15% of that of the lower portion of the arterial chamber.

10. A method of preparing a dialysis machine and a dialyzer for dialysis, comprising;

providing a bloodline set, wherein the bloodline set comprises:

an assembly of tubing defining a flowpath for the blood;

a patient inflow end for receiving a flow of blood from the patient;

a patient outflow end for returning the flow of blood to the patient;

a dialyzer inlet connection and a dialyzer outlet connection for connecting the assembly of tubing respectively to an inlet and an outlet of a dialyzer so that the flowpath passes through the dialyzer;

an arterial chamber arranged between the patient inflow end and the dialyzer inlet connection;

a venous chamber arranged between the dialyzer outlet connection and the patient outflow end; and a first pressure sensing line;

the arterial chamber comprising in a use position: a lower portion, an upper portion, and a central portion arranged between the lower portion and the upper portion;

the first pressure sensing line being fluidly connected to the upper portion of the arterial chamber;

the lower portion of the arterial chamber comprising a shoulder, an arterial chamber inflow connection and an arterial chamber outflow connection so that the flowpath extends through the lower portion of the arterial chamber between the arterial chamber inflow connection and the arterial chamber outflow connection;

the lower portion, the upper portion and the central portion of the arterial chamber each having a corresponding maximum internal section area defined in a horizontal plane in the use position;

wherein the maximum internal section area of the lower portion of the arterial chamber is greater than that of the central portion of the arterial chamber; and and the bloodline set contains both a gas, which fills the upper portion of the arterial chamber and an upper part of the central portion of the arterial chamber, and a priming liquid which fills the lower portion of the arterial chamber and a lower part of the central portion of the arterial chamber to define a liquid/gas interface in the central portion of the arterial chamber;

connecting the bloodline set to a dialysis machine and to a dialyzer, wherein the first pressure sensing line is connected to a pressure sensor of the dialyzer; and filling the flowpath with the priming liquid to establish a primed condition wherein the priming liquid fills the lower portion of the arterial chamber and part of the central portion of the arterial chamber to define the liquid/gas interface in the central portion of the arterial chamber.

11. A method according to claim 10, wherein the venous chamber is substantially completely filled with the priming liquid.

12. A method according to claim 10, wherein the bloodline set is connected to the patient and blood is introduced into the flowpath to fill the lower portion of the arterial chamber leaving a plug of priming liquid in the lower part of the central portion of the arterial chamber.

13. A method of dialysis, including:

providing a bloodline set, wherein the bloodline set comprises:

an assembly of tubing defining a flowpath for the blood;

a patient inflow end for receiving a flow of blood from the patient;

a patient outflow end for returning the flow of blood to the patient;

a dialyzer inlet connection and a dialyzer outlet connection for connecting the assembly of tubing respectively to an inlet and an outlet of a dialyzer so that the flowpath passes through the dialyzer;

an arterial chamber arranged between the patient inflow end and the dialyzer inlet connection;

a venous chamber arranged between the dialyzer outlet connection and the patient outflow end; and a first pressure sensing line;

the arterial chamber comprising in a use position: a lower portion, an upper portion, and a central portion arranged between the lower portion and the upper portion;

the first pressure sensing line being fluidly connected to the upper portion of the arterial chamber;

the lower portion of the arterial chamber comprising a shoulder, an arterial chamber inflow connection and an arterial chamber outflow connection so that the flowpath extends through the lower portion of the arterial chamber between the arterial chamber inflow connection and the arterial chamber outflow connection;

the lower portion, the upper portion and the central portion of the arterial chamber each having a corresponding maximum internal section area defined in a horizontal plane in the use position;

wherein the maximum internal section area of the lower portion of the arterial chamber is greater than that of the central portion of the arterial chamber;

connecting the bloodline set to a dialysis machine and to a dialyzer, wherein the first pressure sensing line is connected to a pressure sensor of the dialyzer, filling the flowpath with a priming liquid to establish a primed condition wherein the bloodline set contains both a gas, which fills the upper portion of the arterial chamber and an upper part of the central portion of the arterial chamber, and the priming liquid which fills the lower portion of the arterial chamber and a lower part of the central portion of the arterial chamber to define a liquid/gas interface in the central portion of the arterial chamber; and then connecting the bloodline set to the patient and introducing blood into the flowpath to fill the lower portion of the arterial chamber leaving a plug of priming liquid in the lower part of the central portion of the arterial chamber; and then circulating the blood through the flowpath, wherein the blood is deflected by the shoulder so as to flow through the lower portion of the arterial chamber beneath the plug of priming liquid.

14. A method according to claim 13, wherein the blood is deflected by the shoulder to form an eddy in the lower portion of the arterial chamber.

15. A method according to claim 13, wherein the blood is deflected by the shoulder to flow across the aperture to form a stacked series of eddies in the plug of priming liquid above the aperture.

16. A method according to claim 13, wherein the venous chamber is substantially completely filled with blood.

17. A bloodline set for conveying blood to and from a patient via a dialyzer, the bloodline set comprising:

an assembly of tubing defining a flowpath for the blood;

a patient inflow end for receiving a flow of blood from the patient;

a patient outflow end for returning the flow of blood to the patient;

a dialyzer inlet connection and a dialyzer outlet connection for connecting the assembly of tubing respectively to an inlet and an outlet of a dialyzer so that the flowpath passes through the dialyzer;

an arterial chamber arranged between the patient inflow end and the dialyzer inlet connection;

a venous chamber arranged between the dialyzer outlet connection and the patient outflow end; and a first pressure sensing line;

the arterial chamber comprising in a use position: a lower portion, an upper portion, and a central portion arranged between the lower portion and the upper portion;

the first pressure sensing line being fluidly connected to the upper portion of the arterial chamber;

the lower portion of the arterial chamber comprising a shoulder, an arterial chamber inflow connection and an arterial chamber outflow connection so that the flowpath extends through the lower portion of the arterial chamber between the arterial chamber inflow connection and the arterial chamber outflow connection;

the lower portion, the upper portion, and the central portion of the arterial chamber each having a corresponding maximum internal section area defined in a horizontal plane in the use position;

wherein the maximum internal section area of the lower portion of the arterial chamber is greater than that of the central portion of the arterial chamber;

the central portion of the arterial chamber opens into the lower portion of the arterial chamber at an aperture, and the shoulder is arranged to deflect blood flowing in use through the lower portion of the arterial chamber from the inflow connection to the outflow connection below a plug of priming liquid in a lower part of the central portion of the arterial chamber to flow across the aperture to form a dynamic interface between the blood and the priming liquid; and wherein the aperture forms a neck, which in the use position defines a reduced horizontal section area relative to the lower portion of the arterial chamber and the central portion of the arterial chamber.

18. A bloodline set according to claim 17, wherein the shoulder is arranged to position the dynamic interface at the aperture so that the blood flowing in use across the aperture induces a stacked series of eddies in the priming liquid in the lower part of the central portion of the arterial chamber.

* * * * *